United States Patent [19]
Burrows et al.

[11] Patent Number: 6,117,138
[45] Date of Patent: Sep. 12, 2000

[54] INSTRUMENTS FOR FORMING BONY CAVITY FOR IMPLANTABLE FEMORAL, HIP PROSTHESIS

[75] Inventors: James W. Burrows, Cedar Park; Erin M. Johnson, Round Rock, both of Tex.

[73] Assignee: Sulzer Orthopedics Inc., Austin, Tex.

[21] Appl. No.: 09/293,187

[22] Filed: Apr. 16, 1999

[51] Int. Cl.[7] ..................................................... A61F 2/46
[52] U.S. Cl. ............................................. 606/80; 606/86
[58] Field of Search .................................. 606/80, 81, 86

[56] References Cited

U.S. PATENT DOCUMENTS

| | | | |
|---|---|---|---|
| 4,135,517 | 1/1979 | Reale | 606/86 |
| 5,607,431 | 3/1997 | Dudasik et al. | 606/80 |
| 5,634,927 | 6/1997 | Houston et al. | 606/80 |
| 5,704,940 | 1/1998 | Garosi | 606/80 |
| 5,733,292 | 3/1998 | Gustilo et al. | 606/86 |
| 5,776,136 | 7/1998 | Sahay et al. | 606/80 |
| 5,800,556 | 9/1998 | Sanders et al. | 606/81 |
| 5,814,049 | 9/1998 | Pratt et al. | 606/80 |
| 5,885,295 | 3/1999 | McDaniel et al. | 606/86 |
| 5,908,423 | 6/1999 | Kashuba et al. | 606/80 |
| 5,980,526 | 11/1999 | Bryant et al. | 606/80 |

FOREIGN PATENT DOCUMENTS

| | | | |
|---|---|---|---|
| 092003993 | 3/1992 | WIPO | 606/89 |

OTHER PUBLICATIONS

Aaron A. Hofmann, M.D., Intermedics Orthopedics, "Natural Hip System" Surgical Technique, pp. 1–30.

Primary Examiner—Paul J. Hirsch
Attorney, Agent, or Firm—Philip S. Lyren; Kenneth S. Barrow

[57] ABSTRACT

A variety of surgical instruments facilitate implantation of a femoral stem component of an implantable prosthesis. A skeletal member is prepared by securing a reamer in the member. A broach is mounted on the reamer for broaching the member. A variety of adapters are selectively used with a head trial to check for location of the head trial. After trial placement is satisfactory, the instruments are removed so that the prosthesis can be implanted.

22 Claims, 4 Drawing Sheets

INSTRUMENTS FOR FORMING BONY CAVITY FOR IMPLANTABLE FEMORAL, HIP PROSTHESIS

BACKGROUND

The disclosures herein relate generally to implantable prostheses for replacing human skeletal joints, and more particularly to surgical instruments useful for implanting orthopedic prostheses that restore the articulating surfaces of the human hip joint.

Implantable orthopedic prostheses, in one form, comprise manufactured replacements for the ends and articulating surfaces of the bones of the skeleton. Such prostheses are implanted to repair or reconstruct all or part of an articulating skeletal joint that if functioning abnormally due to disease, trauma, or congenital defect. Among the various articulating skeletal joints of the human body that are eligible to be fitted with implantable orthopedic prostheses, the hip joint is one of the joints most often treated with such prostheses. The hip joint is a major weight bearing joint and degenerates relatively quickly in case of abnormality. Also, the hip joint plays a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

As used herein, the words proximal and distal are terms of reference that indicate a particular portion of a prosthesis component according to the relative disposition of the portion when the component is implanted. "Proximal" indicates that portion of a component nearest the torso, whereas, "distal" indicates that portion of the component farthest from the torso. Directional terms of reference used herein include superior, inferior, anterior, posterior, medial and lateral, which are used according to their commonly understood anatomical meanings. More particularly, with regard to a person in a standing position, superior means upward, inferior means downward, anterior means forward, posterior means rearward, medial means inwardly from the side toward the center of the body, and lateral means outwardly from the center of the body toward the side.

One or both of the articulation surfaces of the hip joint may fail to act properly, requiring the defective natural articulation surface to be replaced with a prosthetic articulation surface provided by an implantable prosthesis. To fit defects of varying scope, while allowing healthy portions of the hip joint to be conserved, a range of types of orthopedic implants is available. The range extends from total hip prosthesis systems for replacing the articulation surfaces of both the femur and the pelvis, to less comprehensive systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled to suit the anatomical needs of the patient. A so-called "bipolar" hip prosthesis includes only femoral stem and head components. The femoral part of the hip joint is replaced with a femoral stem supporting an artificial femoral head. The latter includes an inner head, fixed to the femoral stem, that articulates within an outer head. The outer head articulates directly against the natural acetabulum. Similarly, a so-called "unipolar" hip prosthesis also includes only femoral stem and head components. The femoral part of the hip joint is replaced with a femoral stem supporting an artificial femoral head. The femoral head articulates directly against the natural acetabulum while remaining fixed relative to the femoral stem.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint. One common type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. The acetabular shell includes a concave distal surface between the apex and annular rim that defines a shell cavity having an opening at the rim of the cup for receiving the bearing insert. The bearing insert has a generally convex proximal surface for receipt and fixation within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component. The acetabular shell can be affixed to the acetabular bone by bone screws or bone cement. If bone screws are elected, the screws are driven into the bone through the screw holes before the bearing insert is placed into the shell. The shell also can be affixed by a combination of a bone screws and bone cement.

The femoral stem component typically is constructed as an integral unit having a distal stem, a proximal body and neck. The distal stem is relatively elongated and generally cylindrical or slightly conical and sized to fit within the relatively narrow intra medullary canal near the proximal end of the femur. The proximal body extends superiorly from the proximal end of the distal stem and is sized to fit within and substantially fill the expanded intramedullary canal at the proximal end of the femur. The neck extends superiorly and medially from the proximal body at an angle of about 45°. The orientation of the neck is designed to replicate the natural orientation of the natural neck of the femur. The proximal end of the neck typically is configured as a male conical taper, or Morse taper, for frictionally interlocking with a mating female conical taper formed in the prosthetic femoral head. The femoral stem can be affixed to the femoral bone surrounding the intramedullary canal by bone cement and rely on bone growth adjacent the implant to secure the implant in place.

The femoral head component is configured substantially as a polished sphere having a blind hole therein shaped as a female conical taper, or Morse taper, for frictionally interlocking with the male conical taper of the neck. The femoral head can also include an integral boss surrounding the blind hole and extending from the head, permitting the offset of the head relative to the femoral stem to be increased.

To implant the femoral stem component, a typical surgical procedure involves resecting the natural neck and head of the proximal femur by performing an osteotomy along a plane oriented substantially perpendicular to the axis of the natural neck. The natural head and neck is removed, exposing the proximal medullary canal of the femur. Specially configured instruments are used to remove cancellous bone from the proximal intramedullary canal and shape a cavity within the cancellous bone that is closely complementary to the external shape of the femoral component. If permitted by the patient's anatomy, it is desirable to enlarge the cavity to the inner wall of the cortical bone and use a prosthesis large enough to engage the cortical bone. This provides secure fixation of and support for the femoral stem.

The cavity that is to be formed in the proximal intramedullary canal is generally elongated and cylindrical or slightly conical at the distal end, and generally oval or trapezoidal in cross-section and tapered longitudinally at the proximal end. To form such a cavity, it is common to employ a rotary reamer to ream the distal portion of the cavity. The rotary reamer is then withdrawn and a broach, shaped like the proximal portion of the femoral component, is repeatedly driven into the proximal intramedullary canal. The broach usually has a stem extension that extends into the previously reamed distal portion of the cavity to serve as a pilot to guide the broach, the proximal portion of which is fitted with cutting surfaces. Often, the pilot stem pistoning in the reamed distal portion of the cavity does not provide enough directional stability to assure that the broached proximal portion of the cavity is well aligned with the reamed distal portion of the canal. The result is a cavity that may not conform as closely to the external shape of the femoral implant as desired.

Prior to implanting the femoral stem, it is useful for the surgeon to be able to confirm that the bone cavity has been reamed to the proper depth. The provides assurance that the center of rotation of the femoral head will be properly located to restore the hip joint to an anatomically correct condition. One method of confirmation is to withdraw the broach and insert a trial femoral stem component into the reamed and broached cavity, and to perform a trial reduction of a joint using a trial femoral head on the trial stem. If the trial reduction indicates that further broaching or reaming of the cavity is required, the trial stem must be withdrawn, the broach must be reinserted, and the procedure must be repeated. To reduce the complexity of the procedure, it is also known to use a broach having means to which a trial femoral head can be attached, thereby permitting the trial reduction to be performed while leaving the broach in place to serve as the trial stem.

In U.S. Pat. No. 5,607,431, a surgical instrument system for preparing the medullary canal of the femur for implanting a prosthetic femoral component includes a template to be used in determining osteotomy position from an x-ray. A gauge is provided to locate and mark this position on the anterior femur. A distal reamer having an elongated drive shaft is used to form the canal to receive the distal stem of the femoral component. A metaphyseal template is used to determine the proper anteversion/retroversion and a chisel is used to cut the lateral area of the femur, both of which are guided by the elongated reamer shaft. A proximal broach also guided by the reamer shaft is used to shape the proximal medullary canal.

Therefore, in view of the limitations of past developments, what is needed is improved surgical instrumentation for preparing a bone cavity in the medullary canal of the proximal femur that accurately forms the bone cavity to a shape closely conforming to the shape of the femoral stem prosthesis to be implanted in the cavity.

SUMMARY

One embodiment, accordingly, provides surgical instruments which facilitate implantation of a femoral stem component of an implantable orthopedic hip joint prosthesis. To this end, a skeletal member is prepared for implanting a prosthesis including securing a reamer in the member. A broach is mounted on the reamer for broaching the member. An adapter is used with a head trial to check for location of the head trial. After trial placement is satisfactory, the instruments are removed so that the prosthesis can implanted.

A principal advantage of these embodiments is that they include a system and components which provide correlation between the reamer, the broach and the calcar planing such that the reamer and broach can be used for trial reduction, then removed so that the implant can be inserted. As a result, all reaming, broaching and planing is done relative to one landmark, or reference, i.e. the reamer. In addition, trial reduction may be accomplished before or after broaching as desired.

BRIEF DESCRIPTION OF THE DRAWING FIGURES

DETAILED DESCRIPTION

Figure 1:
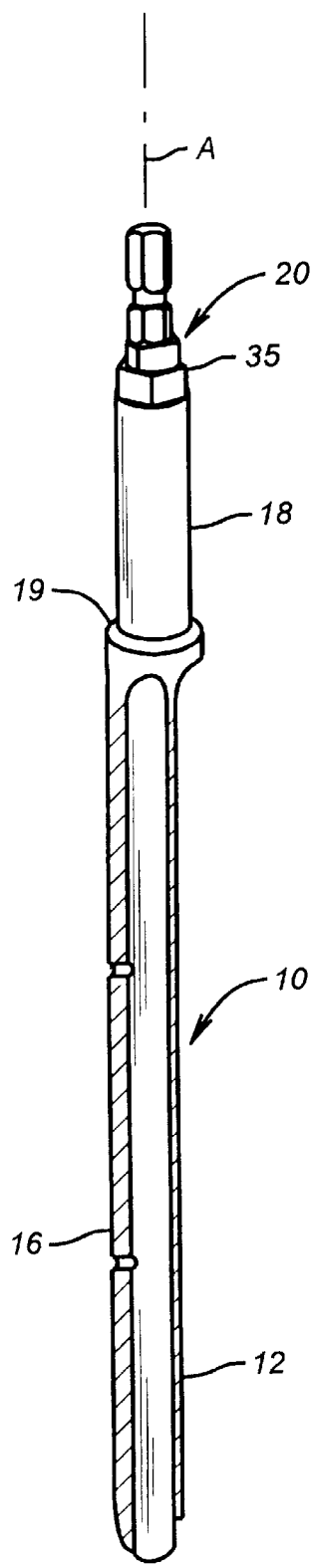
FIG. 1 is a perspective view illustrating an embodiment of a reamer.

In FIG. 1, a reamer, 10 is disclosed and includes a distal portion 12 which includes a cutting portion 16 having cutting teeth or other appropriate cutting surfaces thereon for effectively reaming cancellous bone. Reamer 10 is inserted within the intramedullary canal of the proximal femur and rotated using a suitable rotary power tool. The external profile of cutting portion 16 corresponds to the external profile of the distal stem portion of the femoral stem implant. A cylindrical shaft 18 extends superiorly from a shoulder 19 adjacent cutting portion 16 along an axis of rotation, designated A, of reamer 10. Shaft 18 has a diameter that is smaller than the diameter of at least that region of the cutting portion 16 immediately adjacent shaft 18. A proximal end 20 of shaft 18, is configured to have a polygonal cross-section, hexagonal as preferred, providing a standardized interface to fit and be driven by a selected popular rotary power tool (not shown). A land 35 is formed between shaft 18 and proximal end 35.

Figure 2:
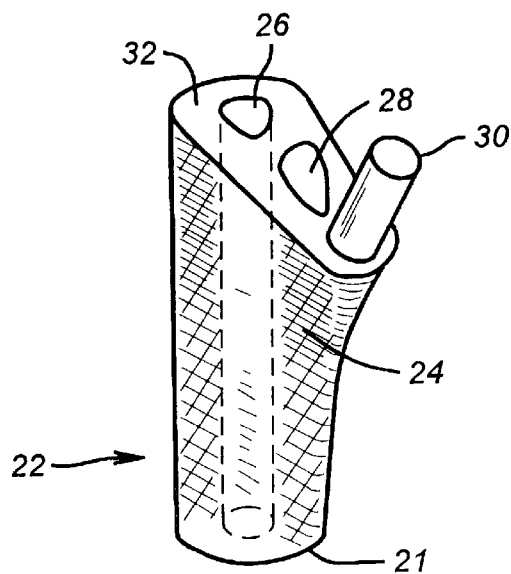
FIG. 2 is a perspective view illustrating an embodiment of a broach.

A proximal broach 22 FIG. 2, includes a cutting portion 24 having cutting teeth or other appropriate cutting surfaces thereon for effectively broaching cancellous bone. Broaching is effected by driving proximal broach 22 in the inferior direction in axial alignment with the axis of rotation of distal reamer 10. A cylindrical bore 26 extending through proximal broach 12 in the superior-inferior direction has a diameter slightly greater than the diameter of shaft 18 of distal reamer 10 to permit close sliding and rotating displacement between shaft 18 and bore 26 such that an inferior end 21 of broach 22 can seat on shoulder 19 of reamer 10. The proximal end of proximal broach 12 is provided with a recess 28 and pin 30 disposed on an angled proximal planar surface 32 to serve as an interface to which a driving tool, not shown, can be locked. Mallet blows directed to a superior end of the driving tool, when locked to the proximal broach 22, permits broach 22 to be driven in the inferior direction. The driving tool, when so locked to the broach 22 can also be used to withdraw broach 22 from the broached bone cavity. The external profile of cutting portion 24 corresponds to the external profile of the proximal body of the femoral stem implant.

Figure 3:
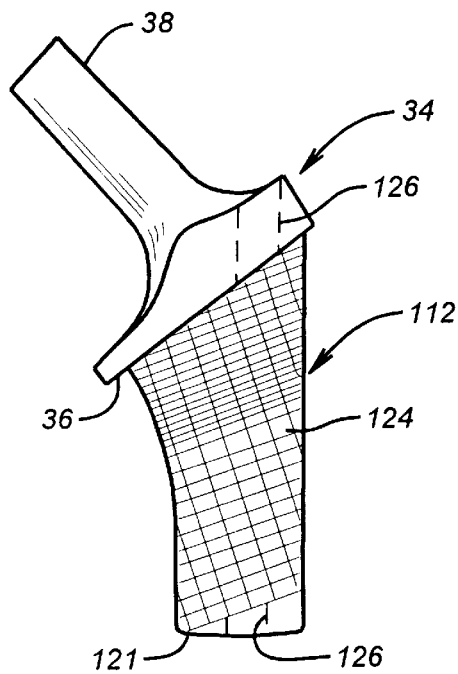
FIG. 3 is a side view illustrating an embodiment of a broach including an integral head trial adapter.

In FIG. 3, a proximal broach 112, similar to that described above, includes a cutting portion 124 having cutting teeth or other appropriate cutting surfaces thereon for effectively cutting cancellous bone. In addition, broach 112 also includes an integral head trial adapter 34 having a collar surface 36 disposed at an appropriate angle and location, and a neck 38 also disposed at an appropriate angle to reproduce the locations of the collar and neck of the femoral stem implant. A cylindrical bore 126 extending through proximal broach 112 and head trial adapter 34 in the superior-inferior direction, has a diameter slightly greater than the diameter of shaft 18 of distal reamer 10 to permit close sliding and rotating displacement between shaft 18 and bore 126 such that a terminal end 121 of broach 112 can seat on shoulder 19 of reamer 10, FIG. 1.

Figure 4:
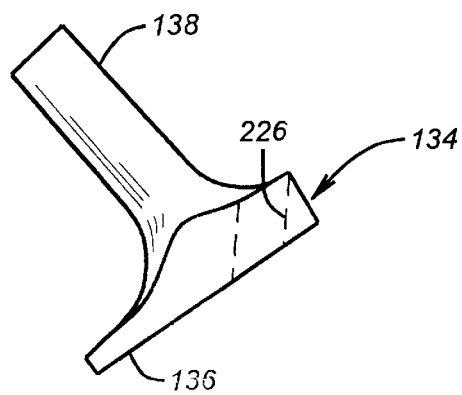
FIG. 4 is a side view illustrating an embodiment of a head trial adapter.

In FIG. 4, a separate head trial adapter 134 is provided with collar surface 136 disposed at an appropriate angle and location, and a neck 138 also disposed at an appropriate angle to reproduce the locations of the collar and neck of the femoral stem implant. A bore 226, extending through head trial adapter 134, in the superior-inferior direction, is sized to permit head trial adapter 134 to seat on land 35 formed adjacent proximal end 20 of reamer 10, FIG. 1.

Figure 5:
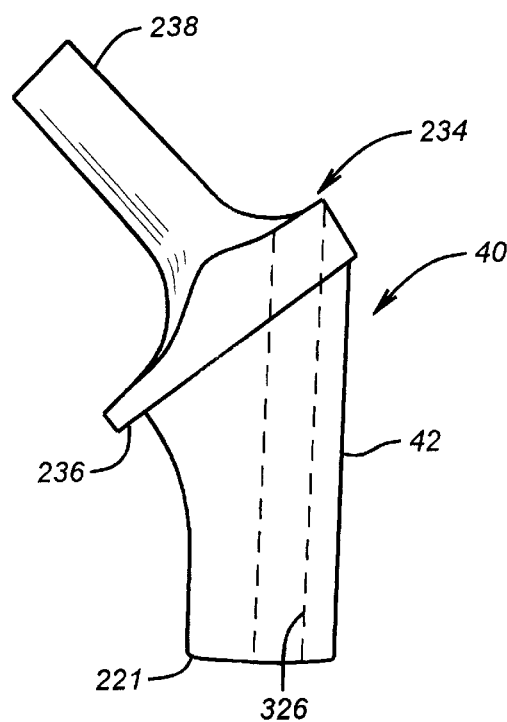
FIG. 5 is a side view illustrating an embodiment of a body trial adapter.

In FIG. 5, a body trial adapter 40 includes a proximal body portion 42, and an integral head trial adapter 234 having a collar surface 236 disposed at an appropriate angle and location, and a neck 238 also disposed at an appropriate angle to reproduce the locations of the collar and neck of the femoral stem implant. A cylindrical bore 326, extending through body trial adapter 40 and head trial adapter 234 in the superior-inferior direction, has a diameter slightly greater than the diameter of shaft 18 of distal reamer 10 to permit close sliding and rotating displacement between shaft 18 and bore 326 such that terminal end 221 of body trial adapter 40 can seat on shoulder 19 of reamer 10, FIG. 1.

Figure 6:
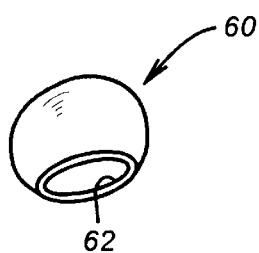
FIG. 6 is a perspective view illustrating an embodiment of a head trial.

A head trial 60, FIG. 6, can be applied to the various necks 38, 138 and 238, FIGS. 3–5 for trial reduction. Head trial 60 is generally spherical and includes a tapered opening 62 for receiving any one of the necks 38, 138 and 238 being used. Once trial placement is satisfactory, the broach 112, trial head adapter 134 or body trial adapter 234, which respectively carry the necks 38, 138 or 238, is removed for femoral implantation.

Figure 7:
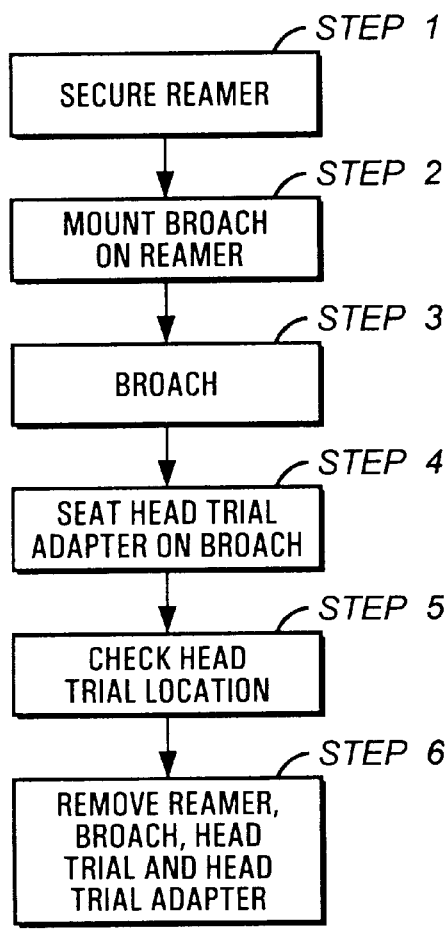
FIG. 7 is a diagram illustrating an embodiment of a method of using surgical instruments.

In operation, there are various optional methods for using the components described above. One method, FIG. 7, includes first securing the reamer 10 in place, step 1, in the intramedullary canal with an appropriate power tool. Broach 22 is placed over shaft 18 of reamer 10, step 2, to broach the canal, step 3, and correctly replicate the desired stem geometry. Head trial adapter 134 may be seated on broach 22, step 4, to check location for head trial 60, step 5. Once trial placement is satisfactory, the reamer 10, head trial adapter 134, broach 22, and head trial 60 are removed, step 6, for femoral implantation.

Figure 8:
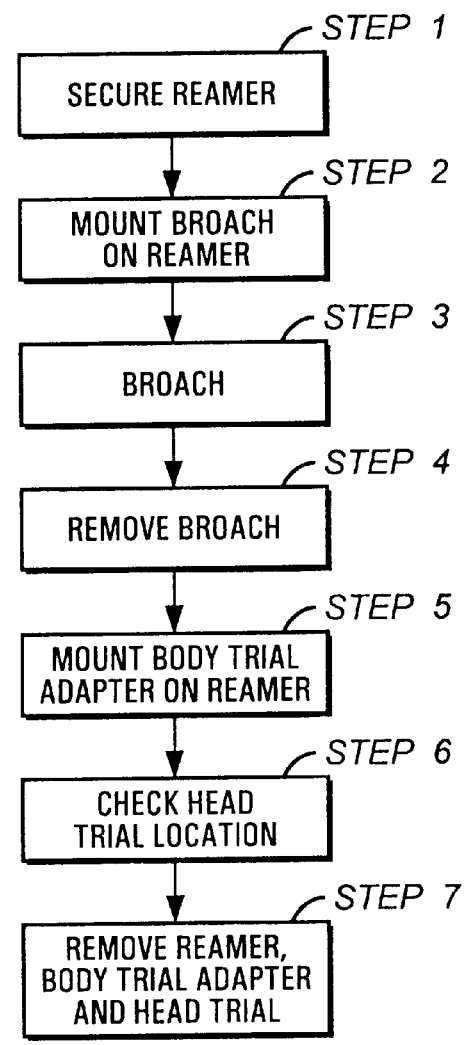
FIG. 8 is a diagram illustrating another embodiment of a method of using surgical instruments.

In another method, FIG. 8, reamer 10 is secured in place, step 1, in the intramedullary canal with the power tool. Broach 22 is placed over the shaft 18 of reamer 10, step 2 to broach the canal, step 3, and correctly replicate the desired stem geometry. Broach 22 is then removed, step 4, from reamer shaft 18. Body trial adapter 40 is then placed over shaft 18 of reamer 10, step 5, to check location for head trial 60, step 6. Once trial placement is satisfactory, the reamer 10 body trial adapter 40 and head trial 60 are removed, step 7, for femoral implantation.

Figure 9:
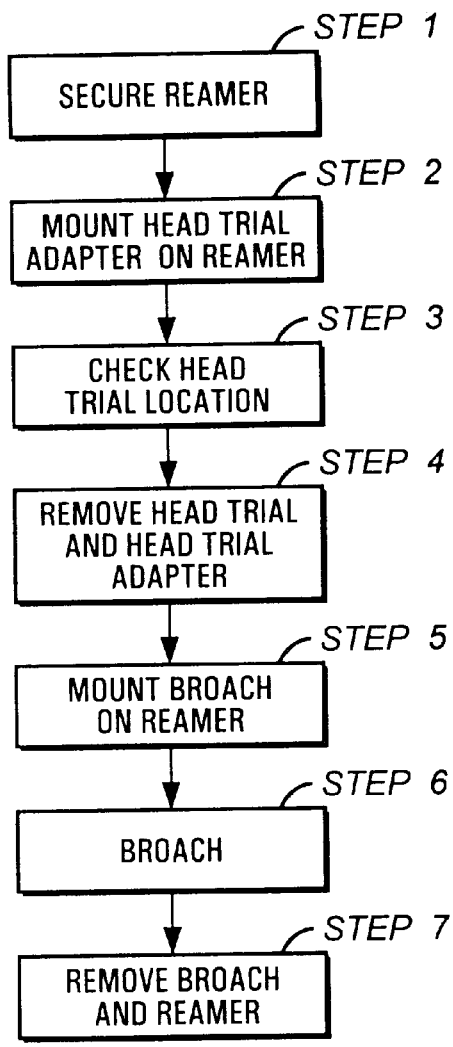
FIG. 9 is a diagram illustrating a further embodiment of a method of using surgical instruments.

Alternatively, FIG. 9, reamer 10 is secured in place, step 1, in the intramedullary canal with the power tool. Head trial adapter 134 is seated on land 35 of shaft 18, step 2, to check location for head trial 60, step 3. Head trial adapter 134 and head trial 60 are then removed, step 4, and broach 22 is placed over shaft 18 of reamer 10, step 5, to broach the canal, step 6, and correctly replicate the desired geometry. Once broaching is complete, broach 22 and reamer 10 are removed, step 7, for femoral implantation.

Figure 10:
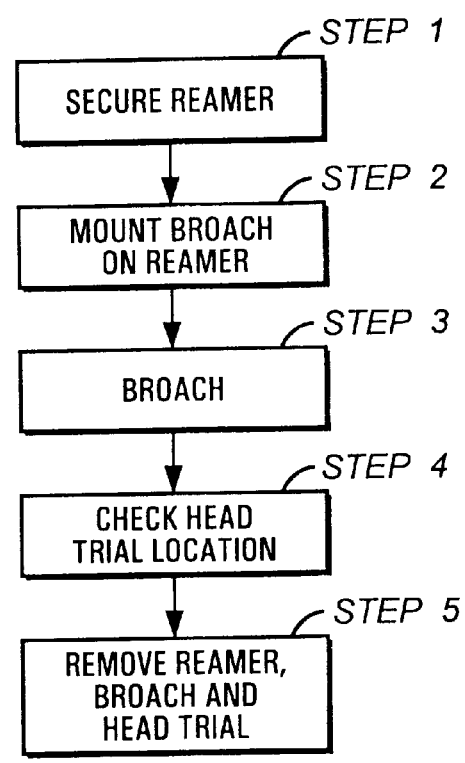
FIG. 10 is a diagram illustrating an additional embodiment of a method of using surgical instruments.

Another option, FIG. 10, secures reamer 10 in place, step 1, in the intramedullary canal with the power tool. Proximal broach 112, including head trial adapter 34, is placed over shaft 18 of reamer 10, step 2, to broach the canal, step 3, and correctly replicate the stem geometry, and also to check location for head trial 60, step 4. Once trial placement is satisfactory, the reamer 10, proximal broach 112 and head trial 60 are removed, step 5, for femoral implantation.

As a result, one embodiment provides a method of preparing a skeletal member for implanting a prosthesis. A reamer is secured in the member. A broach is mounted on the reamer for broaching the member. The broach includes a head trial adapter formed thereon to check for location of a head trial. After trial placement is satisfactory, the reamer, broach and head trial are removed to permit implantation of the prosthesis.

Another embodiment includes securing the reamer in the member and mounting a broach on the reamer for broaching the member. A separate head trial adapter is seated on the broach to check location for a head trial. After trial placement is satisfactory, the reamer, the head trial adapter, the broach and the head trial, are removed to permit implantation of the prosthesis.

A further embodiment includes securing the reamer in the member and mounting a broach on the reamer for broaching the member. The broach is then removed and a body trial adapter is mounted on the reamer to check for location of a head trial. After trial placement is satisfactory, the reamer, the body trial adapter and the head trial are removed to permit implantation of the prosthesis.

Still further embodiment provides securing the reamer in the member and mounting a head trial adapter on the reamer to check location of the head trial. The head trial and the head trial adapter are removed and a broach is mounted on the reamer for broaching the member. After trial placement is satisfactory, the reamer and broach are removed to permit implantation.

An additional embodiment provides a set of instruments for preparing a bone cavity of an implantable prosthesis. A reamer includes cutting members at a first end and a shaft at a second end. A first proximal broach includes a receiver for mounting the broach on the shaft. A second proximal broach includes a receiver for mounting on the shaft and a head trial adapter is formed thereon having a neck extending therefrom. A separate head trial adapter has a neck extending therefrom and includes a receiver for mounting the adapter on the shaft. A body trial adapter includes a receiver for mounting the body trial adapter on the shaft and a head trial adapter is formed thereon having a neck extending therefrom. A head trial has a receiver for mounting on any of the second proximal broach, the separate head trial adapter, and the body trial adapter.

A further added embodiment provides a surgical device for preparing a bone cavity for an implantable femoral hip prosthesis. A reamer includes cutting members at a first end and a shaft at a second end. A plurality of components are selectively mounted on the shaft of the reamer which includes a first proximal broach having a receiver for engaging the shaft; a second proximal broach having a receiver for engaging the shaft and a head trial adapter formed thereon including a neck extending therefrom; a separate head trial adapter having a neck extending therefrom and a receiver for engaging the shaft; a body trial adapter having a receiver for engaging the shaft and a head trial adapter formed thereon including a neck extending therefrom; and a head trial having a substantially spherical body and a receiver for engaging the neck of any of the second proximal broach, the separate head trial, and the body trial adapter.

As it can be seen, the principal advantages of these embodiments are that they include a system and components which provide correlation between a reamer, a broach, a head trial adapter either used separately or in combination with a broach or a body trial, and a head trial. Thus, several combinations are provided to be used for trial reduction. As a result, all reaming, broaching and trial reduction is accomplished relative to the reamer as a landmark reference.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A method of preparing a skeletal member for implanting a prosthesis comprising the steps of:
   securing a reamer in the member;
   mounting a broach on the reamer and broaching the member, the broach including a head trial adapter formed thereon to check for location of a head trial; and
   after trial placement is satisfactory, removing the reamer, the broach and the head trial to permit implantation.

2. The method as defined in claim 1 wherein the step of mounting the broach includes the step of engaging the broach with a shoulder formed on the reamer.

3. A method of preparing a skeletal member for implanting a prosthesis comprising the steps of:
   securing a reamer in the member;
   mounting a broach on the reamer and broaching the member;
   seating a head trial adapter on the broach to check for location of a head trial; and
   after trial placement is satisfactory, removing the reamer, the head trial adapter, broach and the head trial to permit implantation.

4. The method as defined in claim 3 wherein the step of mounting the broach includes the step of engaging the broach with a shoulder formed on the reamer.

5. A method of preparing a skeletal member for implanting prosthesis comprising the steps of:
   securing a reamer in the member;
   mounting a broach on the reamer and broaching the member;
   removing the broach;
   mounting a body trial adapter on the reamer to check for location of a head trial; and
   after trial placement is satisfactory, removing the reamer the body trial adapter and the head trial to permit implantation.

6. The method as defined in claim 5 wherein the step of mounting the broach includes the step of engaging the broach with a shoulder formed on the reamer.

7. The method as defined in claim 6 wherein the step of mounting the body trial adapter includes the step of engaging the body trial adapter with the shoulder.

8. A method of preparing a skeletal member for implanting a prosthesis comprising the steps of:
   securing a reamer in the member;
   mounting a head trial adapter on the reamer to check for location of a head trial;
   removing the head trial and the head trial adapter;
   mounting a broach on the reamer and broaching the member; and
   removing the reamer and the broach to permit implantation.

9. The method as defined in claim 8 wherein the step of mounting the head trial adapter includes the step of engaging the head trial adapter with a land formed on the reamer.

10. The method as defined in claim 9 wherein the step of mounting the broach includes the step of engaging the broach with a shoulder formed on the reamer.

11. A set of instruments for preparing a bone cavity for an implantable prosthesis comprising:
    a reamer including cutting members at a first end and a shaft at a second end;
    a first proximal broach including a receiver for mounting the first proximal broach on the shaft;

a second proximal broach including a receiver for mounting the second proximal broach on the shaft and a head trial adapter formed thereon having a neck extending therefrom;

a separate head trial adapter having a neck extending therefrom and including a receiver for mounting the separate head trial adapter on the shaft;

a body trial adapter including a receiver for mounting the body trial adapter on the shaft and a head trial adapter formed thereon having a neck extending therefrom; and a head trial having a receiver for mounting the head trial on the neck of any of the second proximal broach, the separate head trial adapter, and the body trial adapter.

12. A surgical device for preparing a bone cavity for an implantable femoral hip prosthesis comprising:

a reamer including cutting members at a first end and a shaft at a second end;

a plurality of components for selectively mounting on the shaft of the reamer including:

a) a first proximal broach including a receiver for engaging the shaft;

b) a second proximal broach including a receiver for engaging the shaft and a head trial adapter formed thereon having a neck extending therefrom;

c) a separate head trial adapter having a neck extending therefrom and including a receiver for engaging the shaft;

d) a body trial adapter including a receiver for engaging the shaft and a head trial adapter formed thereon having a neck extending therefrom; and a head trial having a substantially spherical body and a receiver for engaging the neck of any of the second proximal broach, the separate trial head, and the body trial adapter.

13. The surgical device as defined in claim 12 wherein the reamer includes a tool engaging head adjacent the shaft.

14. The surgical device as defined in claim 12 wherein the reamer includes a land between the shaft and the tool engaging head.

15. The surgical device as defined in claim 12 wherein the receiver of the first proximal broach is an elongated bore extending therethrough.

16. The surgical device as defined in claim 12 wherein the receiver of the second proximal broach is an elongated bore extending therethrough.

17. The surgical device as defined in claim 14 wherein the receiver of the separate head trial adapter is a bore for engaging the land.

18. The surgical device as defined in claim 12 wherein the receiver of the body trial adapter is an elongated bore extending therethrough.

19. The surgical device as defined in claim 12 wherein the receiver of the head trial is a blind bore formed therein.

20. The surgical device as defined in claim 12 wherein the reamer includes a shoulder between the first end and the second end providing a seat for the first proximal broach.

21. The surgical device as defined in claim 12 wherein the reamer includes a shoulder between the first end and the second end providing a seat for the second proximal broach.

22. The surgical device as defined in claim 12 wherein the reamer includes a shoulder between the first end and the second end providing a seat for the body trial adapter.

* * * * *